United States Patent
Degieux et al.

(10) Patent No.: US 7,856,705 B2
(45) Date of Patent: Dec. 28, 2010

(54) SYSTEM AND METHOD FOR ASSEMBLING AND INTERCONNECTING FUNCTIONAL COMPONENTS OF AN ACTIVE IMPLANTABLE MEDICAL DEVICE

(75) Inventors: Stephane Degieux, Sceaux (FR); Thierry Legay, Fontenay Las Briis (FR)

(73) Assignee: ELA Medical S.A.S., Montrouge (FR)

( * ) Notice: Subject to any disclaimer, the term of this patent is extended or adjusted under 35 U.S.C. 154(b) by 392 days.

(21) Appl. No.: 11/964,640

(22) Filed: Dec. 26, 2007

(65) Prior Publication Data

US 2008/0184554 A1 Aug. 7, 2008

(30) Foreign Application Priority Data

Dec. 26, 2006 (FR) .................................. 06 11344

(51) Int. Cl.
*H05K 3/00* (2006.01)
(52) U.S. Cl. .............................. 29/829; 29/729; 29/830; 29/831; 29/832
(58) Field of Classification Search .................... 29/729, 29/725, 830, 831, 832, 842, 837, 838, 845, 29/854; 361/749, 684, 679.32; 257/686, 257/778; 439/631, 326
See application file for complete search history.

(56) References Cited

U.S. PATENT DOCUMENTS

| | | | | |
|---|---|---|---|---|
| 5,386,341 A | * | 1/1995 | Olson et al. .................. | 361/749 |
| 6,109,530 A | * | 8/2000 | Larson et al. ................ | 235/492 |
| 6,245,092 B1 | | 6/2001 | Schaldach, Jr. | |
| 6,642,613 B1 | * | 11/2003 | Nguyen et al. ............... | 257/686 |
| 7,134,194 B2 | * | 11/2006 | Brandenburg et al. ......... | 29/832 |

OTHER PUBLICATIONS

Pei Siang S L, et al., "Process Development of a Flip Chip in Package with Anisotropic Conductive Film (ACF) for Lead-free Soldering", 2004 Electronics Packaging Technology Conference, Singapore.
Maattanen J, et. al., "Development of Fine Pitch (54 [mu]m) Flip Chip On Flex Interconnection Process", IEEE Polytronic 2002 Conference.
Kisiel R, "Lead-free Technologies For Electronic Equipment Assembly", Warsaw University of Technology, Warszawa, Poland, Proc. Of SPIE vol. 5125.

* cited by examiner

*Primary Examiner*—Derris H Banks
*Assistant Examiner*—Tai Nguyen
(74) *Attorney, Agent, or Firm*—Orrick Herrington & Sutcliffe, LLP

(57) ABSTRACT

A process for mechanical assembly and electrical interconnection of the functional components of an active implantable medical device. A first step involves preparing an interconnection flex circuit (20) that is able to be electrically and mechanically linked to an electronic circuit module (14), a supply battery (12) and a series of feedthrough terminals (16) of the device, prior to being placed in a common case. The flex circuit has a series of pads (34) for linking to homologous metallizations (46) of the substrate. The mechanical assembling and electrical linking of these pads (34) to the metallizations (46) is performed without either the use of any activation flux or introduction of fusible brazing, and rather by applying an intermediate anisotropic conductive material (38) placed between the pads (34) and metallizations (46), followed by polymerizing this material. The applying and polymerizing are performed under controlled conditions of pressure, temperature and duration.

5 Claims, 2 Drawing Sheets

SYSTEM AND METHOD FOR ASSEMBLING AND INTERCONNECTING FUNCTIONAL COMPONENTS OF AN ACTIVE IMPLANTABLE MEDICAL DEVICE

FIELD OF THE INVENTION

The present invention relates to the technology of manufacturing active implantable medical devices, and more particularly to the assembly of the various functional components constituting such devices that are intended to be incorporated within a common case after being interconnected.

The invention will be mainly described in the context of implantable cardiac pacemakers, but it should be understood that pacemakers represent one embodiment of the invention, and the invention is more generally applicable to a great variety of "Active Implantable Medical Devices" (AIMD) as such devices are described by the Jun. 20, 1990 Directive 90/385/CEE of the Council of the European Communities. This definition includes, in addition to cardiac pacemakers, defibrillators and/or cardioverters, devices such as neurologic devices, pumps for diffusion of medical substances, cochlear implants, implanted biological sensors, etc.

BACKGROUND OF THE INVENTION

These active implantable medical devices (hereinafter referred to as "devices" or "implantable devices") are generally in the form of a case containing a power supply (e.g., a battery) and a hybrid circuit board (hereinafter referred to as "electronic circuit") supporting and interconnecting the various active and passive components, allowing for collecting and analyzing signals, generating electrical pulses, storing data such as medical follow-up information in memory, controlling the device's various functions, etc.

Manufacturing the device usually comprises a series of steps including, first, interconnecting the various functional elements, which are: the battery, the electronic circuit(s) as well as a series of feedthrough terminals intended to be subsequently connected to a corresponding terminal of a connector head. The following step concerns placing the resulting interconnected set of elements inside the case and then adding a connector head. The connector head will be used to ensure the mechanical and electrical connection of the case to external elements, preferably leads for collecting signals and/or delivering pulses.

The interconnection of the foregoing and similar functional elements is usually realized by a flex circuit comprising conductive tracks that are electrically and mechanically linked to the functional elements prior to integrating the functional elements within the case.

U.S. Pat. No. 6,245,092 proposes a cardiac pacemaker made using the flex circuit technology. The conductive tracks are present in the form of printed conductors that have a pad at their extremity which is intended to be linked through a metallization with a corresponding functional element. Brazing, the metallization technique used for the linkage, is a well-known technique providing excellent results in terms of electrical and mechanical performance and long-term reliability.

The use of brazing, typically Tin-lead (Sn—Pb) brazing, however, requires applying a brazing activation flux, followed by a careful cleaning of the substrate so as to remove any remainder of the flux. Until now, chlorofluorocarbon (CFC) based products could very efficiently clean flux from substrates. However, the prohibition against using CFC based products renders this cleaning step more difficult and creates an increased risk of forming metal dendrites resulting from the migration of Sn—Pb alloy to some areas of the substrates that have not have been prepared perfectly.

Moreover, future prohibitions against using brazing allows containing lead exacerbates these difficulties, specifically in the case of AIMD. Indeed, due to the limited room available within the case, the advanced miniaturization of these devices requires creating link pads with a very low pitch (typically 1.47 mm) and very narrow spacing between these pads (the interval between adjacent pads is typically about 250 µm). These problems, resulting from the extreme compactness of circuit area, is further amplified by the reduction of the size of the cases containing these circuits, whose volume has been recently reduced down to 8.5 cc.

U.S. Pat. No. 6,245,092, cited above, incidentally suggests avoiding brazing with lead, and replacing the brazing step with a gluing step. Gluing—which is a well-known and mastered technique in itself—for establishing electrical connections to the components, however, presents some major drawbacks. This technique essentially replaces brazing with a drop of conductive glue (silver glue), deposited on each of the contact pads of the flex printed circuit. This technique therefore requires that an individual deposit one drop onto each contact pad, and is therefore not appropriate for collective processing i.e., automated mass production, as contrasted with brazing (wave brazing for instance), which makes the whole process more complex and expensive.

Further, to avoid the risks of short-circuits between two adjacent pads, particularly if the pads are close to each other, it is highly recommended to deposit an insulating drop into the space separating the two conductive drops deposited on the adjacent pads. This gluing process becomes even more difficult as the circuit dimensions are reduced (pitch and interval between pads), which renders it inappropriate for such applications where advanced miniaturization is an essential requirement. Also, if the glue is in discrete drops, there is always a remaining risk that the silver particles that are in suspension within the conductive drops will migrate to the intermediate non-conductive drop.

OBJECTS AND SUMMARY OF THE INVENTION

It is therefore an object of the present invention to propose a process for the mechanical assembly and electrical linkage of the pads of the interconnection flex circuit to the corresponding metallizations of a functional element of an AIMD, in which the process avoids the use of brazing or gluing techniques, which involve constraints that are difficult to overcome.

It is another object of the present invention to propose a process that is collective, i.e., useful for automated mass production, and does not require any activation flux, cleansing of the surfaces to be linked together, or use of any material containing lead, while responding to the particular requirements of AIMD, such as:

possible implementation with low-volume circuits, packed in high density with an extremely small interval between adjacent link pads;

possible industrialization of the embodiment, through a process that is collective and not operator-dependent;

technique that allows prompt reworking in case a defect is detected during the manufacturing process;

possible utilization with circuits on substrates that diffuse heat, for example, ceramic substrates;

very high reliability (the lifetime of an implant is usually about 10 years and any defect requires the explanation of the device through surgical intervention);

severe mechanical and electrical constraints such as pull out strength, conductivity, isolation, etc.

Advantageously, the present invention is directed to using an anisotropic conductive material that is heat-polymerizable instead of brazing (particularly, Sn—Pb brazing). These anisotropic materials are already well-known for similar purposes, notably for the purpose of interconnecting a flex circuit and a glass substrate, typically for liquid crystal display screens and printed circuit boards. The implementing conditions relating to such known applications are, however, very different from those encountered with AIMD. For example, the components of an AIMD are confined in a far smaller space, and the prior art implementation is done on a support (glass) that does not diffuse heat. Furthermore, until now, this type of connection has been considered, from a long-term point of view, less reliable than Sn—Pb brazing, which is known for excellent aging properties, and therefore provides a level of confidence sufficiently high to be implemented in implantable devices.

For this reason, this technique has so far been restricted to multimedia applications (interconnection of display screens), radiography applications (control screens) and automotive applications (instruments and control panel displays).

More preferably, the present invention proposes, for an active implantable medical device, a process for mechanical assembly and electrical interconnection of functional components of an active implantable medical device intended to be incorporated within a common case after being interconnected. These functional components comprise at least an electronic circuit module, a supply battery and a series of feedthrough terminals able to be linked to a connector head joined to the case.

The process comprises the steps of (i) preparing the interconnection flex circuit electrically and mechanically linked to the respective functional components, wherein the flex circuit comprises a series of pads for linkage to homologous metallizations of one of the functional components, and (ii) mechanical assembly and electrical linkage of the pads of the flex circuit to the homologous metallizations of the functional component.

In a manner characteristic of the invention, the step of mechanical assembly and electrical linkage of the pads of the flex circuit to the homologous metallizations of the functional component is a step (i) essentially not requiring any activation flux or any introduction of fusible brazing in its implementation, and (ii) comprising (a) the placement of an intermediate anisotropic conductive material between the pads and the respective metallizations, and (b) the polymerization of the intermediate anisotropic conductive material, the operations of placement and polymerization executed under controlled pressure, temperature and duration.

The electronic circuit module is preferably a hybrid module with a substrate, such as ceramic material or epoxy, supporting the electronic components. The functional component supporting the metallizations then comprises the module, and the metallizations are formed onto the substrate of this module.

In a preferred embodiment, the step of mechanical assembly and electrical linkage of the pads of the flex circuit to the homologous metallizations of the functional component is performed subsequently to a step of mechanical assembly and electrical linkage of the interconnection flex circuit to the supply battery and feedthrough terminals.

The functional component supporting the metallization can comprise another interconnection flex circuit, and/or a discrete electronic component on which the metallizations are formed.

In a preferred embodiment, the anisotropic conductive material is a film of ACF type. In such a case, the step of mechanical assembly and electrical linkage of the pads of the flex circuit to the homologous metallizations of the functional component comprises (i) a sub-step of pre-tacking by gluing an ACF-type film to the pads, or to the metallizations, and (ii) a sub-step of tacking by positioning the pads vis-à-vis the metallizations, and then polymerizing the pads vis-a-vis the metallizations under pressure, this tacking sub-step being performed under conditions of temperature, duration and pressure higher than those of the pre-tacking step.

In an alternate embodiment, the anisotropic conductive material may be a conductive paste.

BRIEF DESCRIPTION OF THE DRAWINGS

Further features, advantages and characteristics of the present invention will become apparent to a person of ordinary skill in the art in view of the following detailed description of preferred embodiments of the invention, made with reference to the drawings annexed in which like reference characters refer to like elements, and in which.

DETAILED DESCRIPTION OF THE INVENTION

Figure 1:
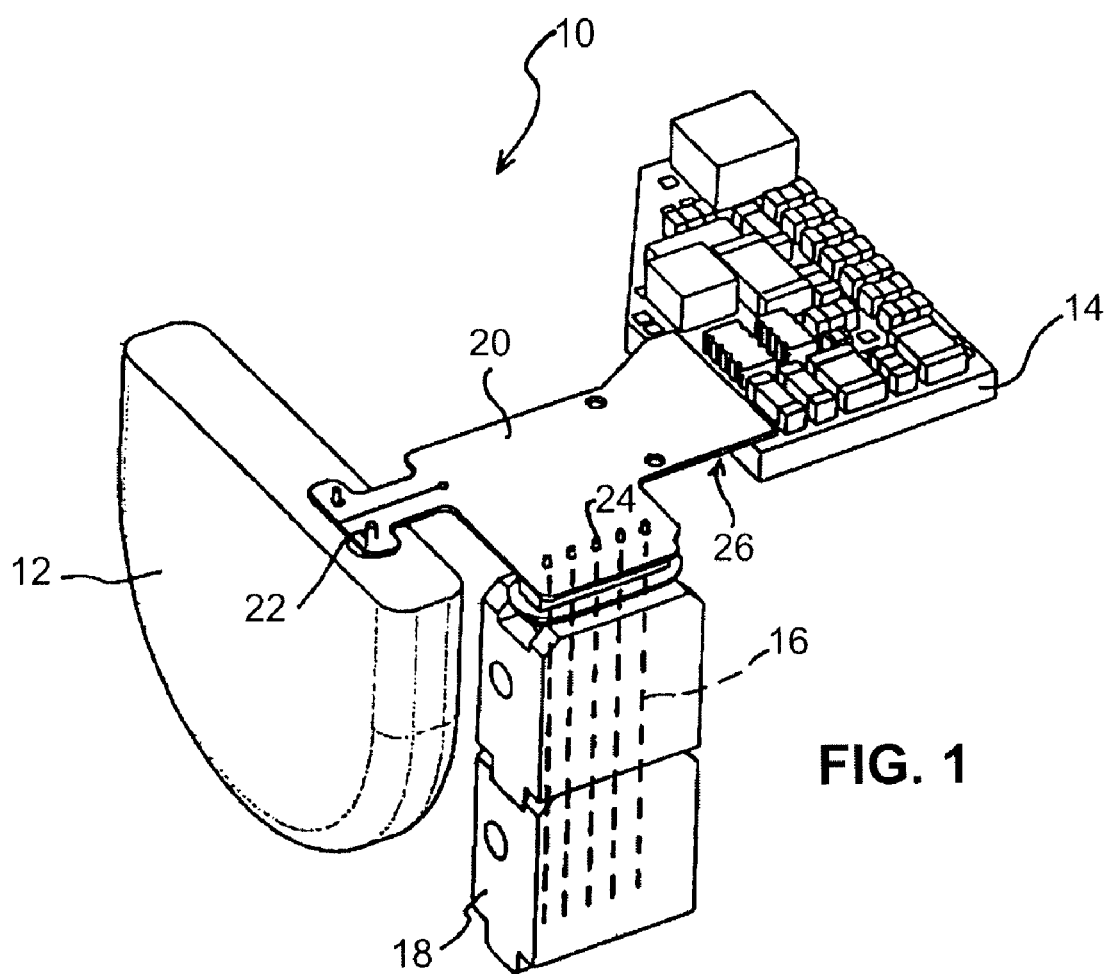
FIG. 1 is an elevated perspective view of the various functional components interconnected by a flex circuit, prior to placing them in the generator's case.

With reference to FIG. 1, the reference 10 designates the whole of the components intended to be placed within the case of a pacemaker or implantable cardioverter defibrillator. These various components, hereinafter generically referred to as "functional components", comprise one or more of a supply battery 12, one or more an electronic circuit module 14 and a series of feedthrough terminals 16, in this case represented as equipped with a cap 18 for their protection until they are placed within the case.

The invention can notably be applied—in a non-limiting manner—to the manufacturing of implantable medical devices marketed by ELA Medical, Montrouge—France, such as the Symphony and ELA Rhapsody brand pacemakers.

The electronic circuit module 14 is, in the illustrated example, a hybrid module comprising a unique substrate supporting the whole of active and passive components of the device. The substrate can notably be made of a multilayer ceramic material receiving, inside appropriate cavities, one or more integrated circuit chips, the cavity being subsequently closed by an insulating resin, so as to provide a surface for receiving the various associated discrete components. The substrate ceramic can be coated with an epoxy resin; in an alternate embodiment, the substrate can be made of an epoxide resin.

The various functional components are interconnected by a flex circuit 20, for example, a polyimide flex circuit, bearing on its surface various metal conductive tracks ensuring the electrical links between the terminals 22 of battery 12, the extremities 24 of terminals 16 and the various link terminals of module 14, that are presented in the form of a series of surface metallizations. These metallizations are intended to be electrically and mechanically linked to the flex circuit 20, level with the interface 26 of circuit 20 with the substrate of module 14.

Figure 2:
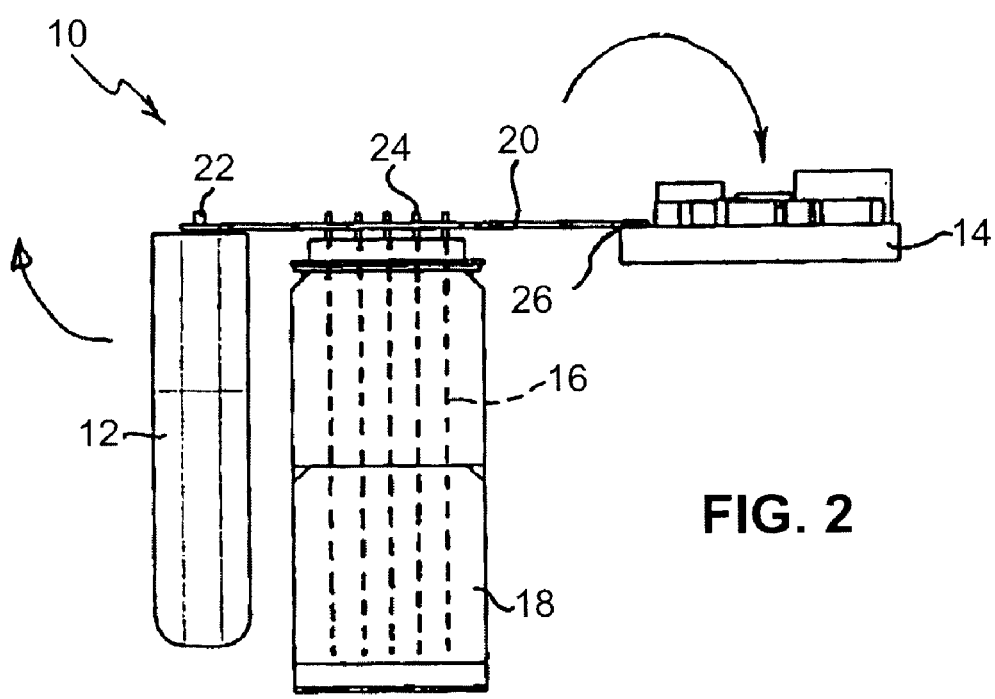
FIG. 2 is front elevation view of FIG. 1.
Figure 3:
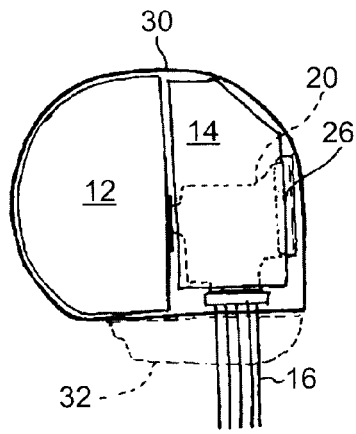
FIG. 3 is a plane view of the functional components after their placing in the generator's case.

Once the linkage of the various functional components to the interconnection flex circuit 20 is realized, the various components are positioned in a common plane, through bending the flex circuit 20, following the arrows illustrated in FIG. 2. The finished configuration is that illustrated in FIG. 3, with the battery 12 approximately lying in the same plane as that of flex circuit 20, and the module 14 turned back against this same circuit 20, which is curved at 180° in the vicinity of interface 26. As for the terminals 16, they are straightened by a quarter-turn relative to their initial position, and spread over the common plane of the other components positioned as explained above.

The various functional components, thus configured, can then be placed in the case 30 of the generator, in as confined a configuration as possible, with a minimum lost volume. In a subsequent step, a connector head 32 will be fitted onto the case 30 and the various conductive organs of the connector will be electrically connected to terminals 16.

Another aspect of the present invention concerns the realization of the electrical and mechanical linkage of flex circuit 20 to the substrate of the electronics module 14 level with the interface 26 of these two elements. It should be understood that insofar as the linkage of battery 12 and terminals 16 to the flex circuit does not raise the same difficulties identified earlier, this linkage, level with the terminals 22 and 24, can be realized in a traditional manner, by brazing. The invention is also applicable to the realization of the links described below and the special advantages should be taken into account.

The extremities of the conductive tracks of the flex circuit 20 shall be electrically and mechanically linked to the homologous metallizations formed on the substrate of module 14, while respecting the various electrical, mechanical, industrial and environmental requirements cited in the introduction of the present disclosure.

The invention proposes, in a characteristic manner, to realize these links through a process of high temperature gluing, under pressure constraints, of the flex circuit to the substrate, with interpositioning of an anisotropic conductive film. Such anisotropic conductive films are well-known in the applications cited above (multimedia, automotive industry, etc.), but, until now, have not been considered in the domain of medical implantable devices, taking into account the much more severe restrictions in terms of aging properties, miniaturization, etc. Anisotropic conductive films are known under the denomination of "ACF films" or "Z-axis conductive films". For example, it is possible to use the ACF-type films marketed by Hitachi Chemical Co., Ltd or any similar film.

Figure 4:
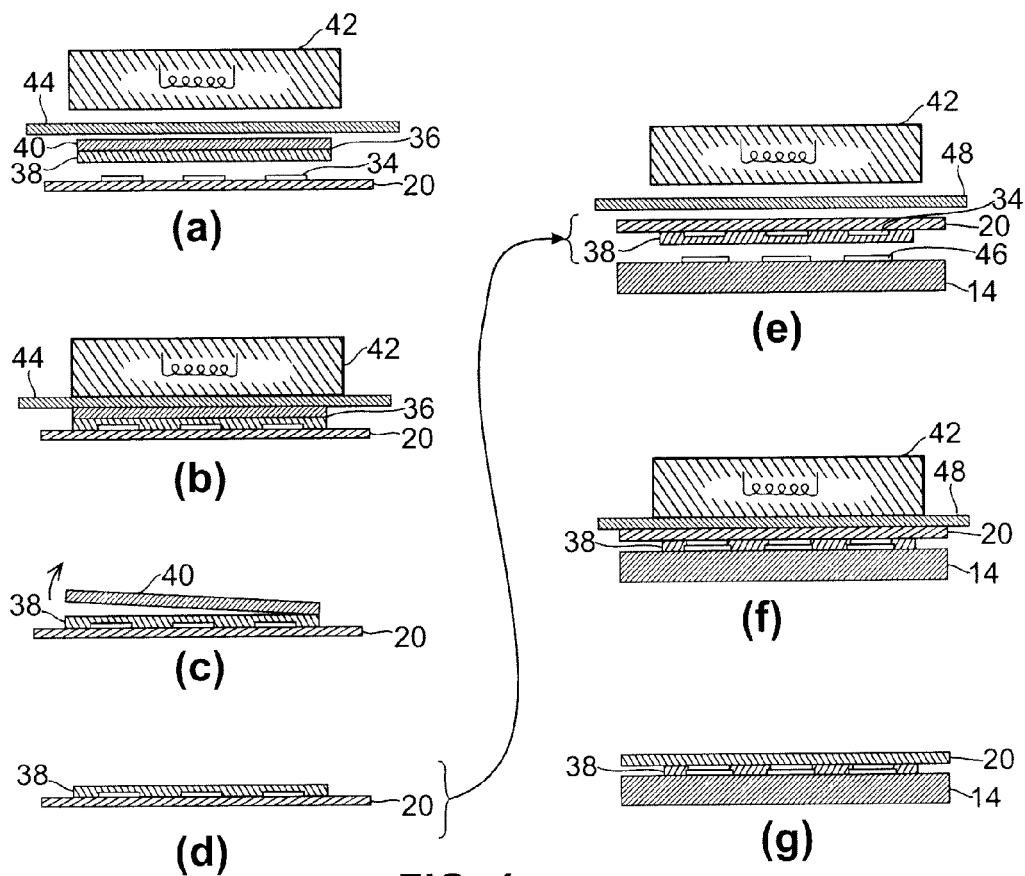
FIG. 4 illustrates a process of pre-tacking and tacking of a typical assembly process in accordance with the present invention.

FIG. 4 illustrates the various successive steps of the process according to this invention, which essentially comprises two phases, so called "pre-tacking" (steps ad) then "tacking" (steps e-g) phases.

The "pre-tacking" phase consists of making an ACF film adhere to one of the two parts to be assembled, such as flex circuit 20 (although substrate 14 could be used instead), as illustrated in FIG. 4.

At step a, the flex circuit 20, which is already linked by brazing to the battery 12 and terminals 16, is positioned by an appropriate tool.

Using the same tool, an ACF film 36 is positioned above flex circuit 20. This film comprises, in a manner known per se, an anisotropic conductive layer (ACF layer) 38 deposited on a protective backing 40 which is, in one example, made of PET. The ACF layer 38 is turned toward the conductive pads 34 of flex circuit 20, and a heating element or thermode 42 is put in the vicinity of the back of the ACF film 36, advantageously with interpositioning of a silicon ribbon 46 so as to absorb the asperities and for a better spreading of heat.

The following step b consists of laminating ACF film 36 on flex circuit 20 by means of heat-adhesion under pressure. The conditions for this step are, for example as follows: heating to a temperature of about 80° C., applying the thermode for a duration of 3 to 5 seconds, and applying pressure of 0.5 to 1.5 MPa. Once this heat-adhesion step has been performed, the following step c involves, after removal of thermode 42 and intermediate ribbon 44, extracting the protective backing 40, so that only the thickness of the ACF film per se 38 remains on the flex circuit 20. The configuration in the end of this pre-tacking phase is as illustrated in FIG. 4.

The following "tacking" phase, corresponds to steps e to g illustrated in FIG. 4. At step e, after the flex circuit 20 equipped with ACF film 38 has been turned back to back, it is placed facing the substrate 14, so that the pads 34 (covered with ACF film 38) of flex circuit 20 are positioned relative to metallizations 46 that are present on the surface of substrate 14. As with step a, the thermode 42 is positioned above the assembly, with interposition of a silicone protective ribbon 48 so as to absorb asperities and provide a better spreading of heat. Step f consists of laminating the assembly, under pressure and high temperature, so as to polymerize the resin of the ACF film. The conditions for this step are, for example: heating to a temperature of about 170° C., applying the thermode for a duration of 10 to 15 seconds, and applying pressure of 2 to 4 MPa.

The final configuration is as illustrated in FIG. 4g.

Figure 5:
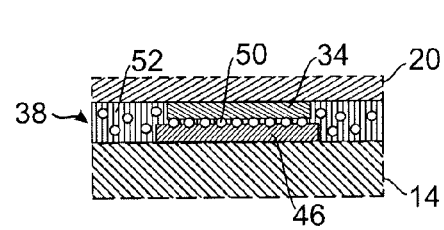
FIG. 5 is a magnified sectional view of Section V of FIG. 4, the conductive interface between flex circuit and substrate of the electronic circuit module.

FIG. 5 shows, in a magnified format, the detail referred to as portion V of FIG. 4g. At the interface between the pads 34 of flex circuit 20 and metallizations 46 of substrate 14, the ACF film 38 contains conductive micro-balls 50 contained within a paste 52. The dimension and concentration of these conductive micro-balls 50 are chosen so as to establish an electrical contact of excellent quality between pad 34 and metallization 46 at the end of the process, at the interface of these two elements.

However, out of this interface, the concentration of micro-balls is not sufficient for them to come into mutual contact, thus preventing any electrical link between flex circuit 20 and substrate 14 (out of the interface between pads and metallizations). One can thus typically obtain a pad/metallization contact impedance lower than 10Ω and a flex circuit to substrate isolation resistance higher than 1 GΩ. These specifications are preserved, even after aging and submission to heat, humidity, etc. constraints, which provide excellent aging properties.

If the temperature/time/pressure profile is defined in a precise and reproducible way for the steps of pre-tacking and tacking, then the process can be industrialized in a perfectly repetitive and reproducible manner. Furthermore, in case of a defect, the product is "reworkable". In a manner similar to a brazed link, a flex circuit that has a defective connection may be replaced by another circuit, after cleaning the hybrid circuit, the operation being carried out through pealing on a heating plate at a temperature of about 125° C.

In an alternate embodiment, it is also possible to replace the use of an ACF ribbon by an anisotropic conductive paste, packaged in a syringe. This paste can then preferably be deposited, at ambient temperature, on sections covering the metallizations of the substrate or conductive pads of the flex circuit, the heat sealing being then performed as described above.

Moreover, the present invention is not limited to the realization of a link between a flex circuit and substrate of a hybrid circuit. It can also be used for linking two flex circuits together, or to an attached discrete component, as such or on a chip carrier.

One skilled in the art will appreciate that the present invention can be practiced by embodiments other than those disclosed, which are presented for purposes of illustration and not limiting.

We claim:

1. A process for mechanical assembly and electrical interconnection of functional components of an active implantable medical device, wherein the functional components include at least one electronic circuit module, a power supply battery, and a series of feedthrough terminals linked to a connector head joined to a common case, and wherein the functional components are integrated in the common case after being interconnected, comprising the steps of:
preparing a flex circuit that is electrically and mechanically linked to the respective functional components, wherein the functional components comprise homologous metallizations, and wherein the flex circuit comprises a series of pads for linking to the homologous metallizations of the functional components; and
mechanically assembling and electrically linking the pads of the flex circuit to the homologous metallizations of each functional component, wherein the step of mechanically assembling and electrically linking the pads of the flex circuit to homologous metallizations of the functional components further comprises applying an intermediate anisotropic conductive material between the pads and the respective homologous metallizations, and polymerizing the intermediate anisotropic conductive material, under controlled conditions of pressure, temperature and duration, wherein:
applying an intermediate anisotropic conductive material further comprises a film of the ACF type; and
mechanically assembling and electrically linking the pads of the flex circuit to homologous metallizations of the functional component further comprises:
a pre-tacking sub-step comprising gluing the ACF film on one of the pads and the homologous metallizations; and
a tacking sub-step comprising positioning the pads vis-a-vis the homologous metallizations, polymerizing the pads vis-a-vis the homologous metallizations under pressure, wherein the tacking sub-step is performed under temperature, duration and pressure conditions higher than those applied for the pre-tacking sub-step.

2. A mechanical assembly comprising functional components, wherein the functional components are integrated in a common case after being interconnected and includes at least one electronic circuit module, a power supply battery, and a series of feedthrough terminals linked to a connector head joined to the common case, the functional components being assembled and interconnected by the process of:
preparing a flex circuit that is electrically and mechanically linked to the respective functional components, wherein the functional components comprise homologous metallizations, and wherein the flex circuit comprises a series of pads for linking to the homologous metallizations of the functional components; and
mechanically assembling and electrically linking the pads of the flex circuit to the homologous metallizations of each functional component, wherein the step of mechanically assembling and electrically linking the pads of the flex circuit to homologous metallizations of the functional components further comprises applying an intermediate anisotropic conductive material between the pads and the respective homologous metallizations, and polymerizing the intermediate anisotropic conductive material, under controlled conditions of pressure, temperature and duration, wherein the electronic circuit module further comprises a hybrid module with a substrate supporting electronic components, and the functional components comprising the homologous metallizations further comprise the electronic circuit module, wherein the homologous metallizations are formed on the substrate of the electronic circuit module.

3. The mechanical assembly of claim 2, wherein the functional components comprising the homologous metallizations further comprise a second interconnection flea circuit on which the homologous metallizations are formed.

4. The mechanical assembly of claim 2, wherein the functional components comprising the homologous metallizations further comprises a discrete electronic component on which the homologous metallizations are formed.

5. The mechanical assembly of claim 2 further comprising:
applying an intermediate anisotropic conductive material further comprises a film of the ACF type; and
mechanically assembling and electrically linking the pads of the flex circuit to homologous metallizations of the functional components further comprises:
a pre-tacking sub-step comprising gluing the ACF film on one of the pads and the homologous metallizations; and
a tacking sub-step comprising positioning the pads vis-a-vis the homologous metallizations, polymerizing the pads vis-a-vis the homologous metallizations under pressure, wherein the tacking sub-step is performed under temperature, duration and pressure conditions higher than those applied for the pre-tacking sub-step.

* * * * *